(12) United States Patent
Sandman et al.

(10) Patent No.: US 7,772,464 B2
(45) Date of Patent: Aug. 10, 2010

(54) AGRONOMICALLY ADAPTED ALFALFA PLANTS WITH HIGH LEVELS OF SOMATIC EMBRYOGENESIS

(75) Inventors: Jay M. Sandman, West Salem, WI (US); David W. Johnson, West Salem, WI (US); Lauren D. Johnson, Woodland, CA (US); Mark E. Darling, Woodland, CA (US); Jonathan M. Reich, Woodland, CA (US)

(73) Assignee: Cal/West Seeds, Woodland, CA (US)

( * ) Notice: Subject to any disclaimer, the term of this patent is extended or adjusted under 35 U.S.C. 154(b) by 691 days.

(21) Appl. No.: 11/436,538

(22) Filed: May 19, 2006

(65) Prior Publication Data

US 2007/0124840 A1 May 31, 2007

Related U.S. Application Data

(60) Provisional application No. 60/682,835, filed on May 20, 2005.

(51) Int. Cl.
*A01H 1/00* (2006.01)
*A01H 5/00* (2006.01)

(52) U.S. Cl. .................. 800/298; 800/260; 435/410

(58) Field of Classification Search ............ 800/260, 800/295, 304; 435/410
See application file for complete search history.

(56) References Cited

U.S. PATENT DOCUMENTS

| 5,324,646 | A | 6/1994 | Buising et al. |
|---|---|---|---|
| 5,731,202 | A | 3/1998 | Buising et al. |
| 5,908,974 | A | 6/1999 | McCaslin |
| 5,994,626 | A | 11/1999 | Buising et al. |
| 6,127,599 | A | 10/2000 | McCaslin |
| 6,143,951 | A | 11/2000 | Cluff et al. |
| 6,359,195 | B1 | 3/2002 | Peterson |
| 6,563,019 | B1 | 5/2003 | Deak et al. |
| 6,566,137 | B1 | 5/2003 | Buising et al. |

OTHER PUBLICATIONS

Chen et al. 1987. Plant Cell, Tissue and Organ Culture 8: 73-81.*
Hanson et al. Crop Science 27: 1084, 1987.*
Bingham et al., "Alfalfa Tissue Culture", pp. 903-929, In Alfalfa and Alfalfa Improvement, Hanson, et al. (ed), American Society of Agronomy, Monograph No. 29 (1988).
Saunders, J.W. and E.T. Bingham, "Production of Alfalfa Plants from Callus Tissue", Crop Science 12(6):804-808 (1972).
Bingham, E.T., et al., "Breeding Alfalfa Which Regenerates from Callus Tissue in Culture", Crop Science 15:719-721 (1975).
Hanson et al., Crop Science 27:1084 (1987).
Ray et al., "Breeding Diploid Alfalfa for Regeneration from Tissue Culture", Crop Science 29:1545-1548 (1989).
Seitz et al., "Interations of Highly Regenerative Genotypes of Alfalfa (*Medicago sative*) and Tissue Culture Protocols", In Vitro Cellular & Developmental Biology 24:1047-1052 (1988).
Fuentes et al., "Embnryogenic response of Mexican alfalfa (*Medicago sativa*) varieties", Plant Cell, Tissue and Organ Culture 34:299-302(1993).
Daniel C.W. Brown, "Germplasm Determination of in Vitro Somatic Embryogenesis in Alfalfa", HortScience 23(3):526-531 (1988).

* cited by examiner

*Primary Examiner*—David H Kruse
*Assistant Examiner*—Keith O. Robinson
(74) *Attorney, Agent, or Firm*—Cooley LLP

(57) ABSTRACT

The invention provides alfalfa plants having adaptation, productivity, winterhardiness, and disease resistance with high levels of somatic embryogenesis. Plants and plant parts of the invention are useful in the efficient development of transgenic alfalfa plants with adaptation, productivity, winterhardiness, and disease resistance.

14 Claims, No Drawings

AGRONOMICALLY ADAPTED ALFALFA PLANTS WITH HIGH LEVELS OF SOMATIC EMBRYOGENESIS

CROSS-REFERENCE TO RELATED APPLICATIONS

This application is entitled to priority pursuant to 35 U.S.C. §119(e) to U.S. provisional patent application No. 60/682,835, which was filed on May 20, 2005, which is incorporated herein in its entirety.

FIELD OF THE INVENTION

This invention relates to the field of alfalfa plants, and more specifically to improved alfalfa plants having increased levels of somatic embryogenesis and methods for producing such plants.

BACKGROUND OF THE INVENTION

All publications and patent applications herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Alfalfa (*Medicago sativa* L.) is an important forage species for hay and pasture, which has been referred to as the "Queen of the Forages" because of its high yields and feeding value. Alfalfa is recognized as the most widely adapted agronomic crop, as an effective source of biological nitrogen ($N_2$) fixation, useful in the improvement of soil tilth, as an important source of protein yield/ha, and as an attractive source of nectar for honeybees. For a comprehensive review of the benefits of alfalfa as an agronomic crop, see Barnes et al., *Highlights in the USA and Canada* 1:2-24, In *Alfalfa and Alfalfa Improvement*, Hanson et al. (ed.), American Society of Agronomy, Monograph No. 29 (1988).

Although alfalfa originated in southwestern Asia, it is well adapted to a wide range of climates and soils in the United States. Alfalfa is classified into fall dormancy groups, numbered 1 to 10, which can be fitted into the plant hardiness zone map. Dormancy group 1 is very dormant and best suited for cold climates (such varieties would stop growing and go dormant over winter), and dormancy group 10 is very non-dormant and suited for very hot climates (such varieties would have high growth rates over a very long growing season and would have relatively high winter activity). For a comprehensive review of geographic adaptation of alfalfa, see Melton et al., *Geographic Adaptation and Cultivar Selection* 20: 595-620, In *Alfalfa and Alfalfa Improvement*, supra. Between 1900 and 1975 more than 160 cultivars were developed for production in North America. Most of the newer cultivars were selected for improved adaptation and multiple pest resistance. For a comprehensive review of the distribution, history and origin of alfalfa, see Michaud et al., *World Distribution and Historical Development* 2:25-91, In *Alfalfa and Alfalfa Improvement*, supra; and, Quiros et al., *The Genus Medicago and the Origin of the Medicago sativa Complex* 3:93-124, In *Alfalfa and Alfalfa Improvement*, supra.

The genus *Medicago* is widely distributed and comprises an array of diverse species that are either annual or perennial. The most recent taxonomic studies of the perennial species concluded that *M. sativa* is polymorphic. Lesins and Gillies (Taxonomy and cytogenetics of *Medicago* 353-386, In *Alfalfa science and technology*, C. H. Hanson (ed.), American Society of Agronomy, (1972)) defined the complex as *M. sativa-falcata-glutinosa*, and Gunn et al. (USDA *Tech. Bull. No.* 1574 (1978)) designated it as the *M. sativa sensu lato* complex.

*M. sativa* plants are autopolyploid organisms, or more specifically, autotetraploids. More specifically, *M. sativa* plants are polysomic polyploid organisms which display tetrasomic inheritance patterns.

Essentially all annual species are cleistogamous and are exclusively self-pollinated. Generally, the perennial species require tripping, as by insect visits to the floral structures, and will set seed from either self or cross-pollination. Crosses can be made among subspecies in the *M. sativa* complexes and between the cultivated tetraploids and wild diploids without special preparation of the parents. For a comprehensive review of the floral characteristics, plant culture, and methods of self-pollinating or hybridizing alfalfa, see D. K. Barnes, *Alfalfa* 9:177-187, In *Hybridization of Crop Plants*, Fehr et al. (ed.), American Society of Agronomy Inc. (1980).

Commercial alfalfa seed may be provided either in a synthetic variety or a hybrid variety. Commercial production of synthetic varieties may include a breeder seed production stage, a foundation seed production stage, a registered seed production stage and a certified seed production stage. Hybrid variety seed production may involve up to three stages including a breeder seed production stage, a foundation seed production stage and a certified seed production stage.

Efforts in developing healthy and productive alfalfa varieties often focus on breeding for disease and stress-resistant cultivars, for example, breeding for persistence, breeding for adaptation to specific environments, breeding for yield per se, and breeding for quality. Success has been attained in breeding for resistance to fungal, bacterial, insect, and nematode pests, including, but not limited to the development of varieties tolerant/resistant to bacterial wilt and common leaf spot (see, e.g., Elgin, Jr., et al., *Breeding for Disease and Nematode Resistance* 827-858, In *Alfalfa and Alfalfa Improvement*, supra) and to the spotted alfalfa aphid and alfalfa weevil (see, e.g., Sorensen et al., *Breeding for Insect Resistance* 859-902, In *Alfalfa and Alfalfa Improvement*, supra). Breeders have had less success in breeding for yield and quality per se (see, e.g., Hill et al., *Breeding for Yield and Quality* 26:809-825, In *Alfalfa and Alfalfa Improvement*, supra), although methods have been developed that help increase productivity and yield (U.S. Pat. No. 4,045,912). Historically, yield and productivity, quality and persistence are objectives of high concern to farmers.

In addition to conventional or classical plant breeding methodology, recombinant DNA technologies exist that allow alfalfa breeders to incorporate novel genes into alfalfa plants. Transgenic plants can now be produced by a variety of different transformation methods including, but not limited to, electroporation; microinjection; microprojectile bombardment, also known as particle acceleration or biolistic bombardment; viral-mediated transformation; and Agrobacterium-mediated transformation. Transgenic alfalfa plants have been produced by many of these methods including, but not limited to, Agrobacterium-mediated transformation (Wang et al., *Australian Journal of Plant Physiology* 23(3): 265-270 (1996); Hoffman et al., *Molecular Plant-Microbe Interactions* 10(3):307-315 (1997); Trieu et al., *Plant Cell Reports* 16:6-11 (1996)) and particle acceleration (U.S. Pat. No. 5,324,646).

Various factors are important for the efficient transformation of crop plants. Of these variables, the ability to regenerate a complete plant from one or multiple cells of transformed explant tissue is one of the most important. Even when transformation has been achieved and is routine for a particular genotype of a crop species, it can still be difficult to transform any genotype of choice within a recalcitrant species. Numerous reports cite differences between genotypes within a species in the ability to regenerate in vitro (e.g. Diertert et al 1982; Christey and Earle, 1991). Such reports indicate that the regeneration processes are genetically controlled.

Alfalfa was one of the first major crop plants to regenerate somatic embryos from tissue culture (Saunders and Bingham, 1972). The ability of an alfalfa genotype to regenerate somatic embryos is believed to be genetically controlled by two genes. Bingham et al. (1975) were able to increase the frequency of plants which regenerate somatic embryos within a population of alfalfa through conventional breeding practices. Much of the published research in alfalfa transformation utilizes the alfalfa clone Regen SY as the source of explant material because of the suitability of this genotype for regeneration. Regen SY is a poorly adapted clone that lacks vegetative vigor, winterhardiness, resistance to many diseases and has a very poor phenotype compared to agronomically elite clones from conventional alfalfa breeding programs.

As demonstrated by this review, there is a real need for alfalfa plants that combine adaptation, productivity, winterhardiness, and disease resistance with high levels of somatic embryogenesis. The present invention provides alfalfa plants selected for improved somatic embryogenesis. The alfalfa plants provided by this invention combine adaptation, productivity, winterhardiness, and disease resistance with high levels of somatic embryogenesis.

SUMMARY OF THE INVENTION

This invention provides agronomically adapted alfalfa plants having improved somatic embryogenesis. In another aspect the present invention provides plants that combine improved somatic embryogenesis with a desirable alfalfa phenotype. In yet another aspect the invention provides alfalfa plants with improved somatic embryogenesis, adaptation, productivity, winterhardiness, and disease resistance. In still another aspect the invention provides a method for producing alfalfa plants with improved somatic embryogenesis comprising identifying and isolating alfalfa plants with the ability to produce somatic embryos and crossing these plants together so as to produce progeny plants with higher levels of somatic embryogenesis than the parental plants.

The invention also provides any of the reproductive and regenerative parts of any of the alfalfa plants of the present invention, including but not limited to plant cells (in vivo and in vitro), cell cultures, plant parts, plant tissues and tissue cultures. Examples of such plant cells, plant tissues or plant parts include but are not limited to pollen, ovary, ovules, cotyledons, seeds, seedlings, leaflets, leaves, petioles, stems, branches, stipules, and the like.

In yet another embodiment, the present invention provides a tissue culture of regenerable cells from the alfalfa plants of the present invention, wherein the tissue regenerates plants having all or substantially all of the morphological and physiological characteristics of the alfalfa plants provided by the present invention. In one such embodiment, the tissue culture is derived from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. In another such embodiment, the present invention includes an alfalfa plant regenerated from the above described tissue culture.

This invention provides the cells, cell culture, tissues, tissue culture, seed, whole plants and plant parts of alfalfa germplasm designated 'CW-R97-037-001' and having ATCC Accession No. PTA-7608.

This invention provides the cells, cell culture, tissues, tissue culture, seed, whole plants and plant parts of alfalfa germplasm designated 'CW-R97-037-005' and having ATCC Accession No. PTA-7607.

This invention also provides a cell, cell culture, tissue and/or tissue culture of regenerable cells, the cells comprising genetic material from the alfalfa germplasm named 'CW-R97-037-001', wherein the cells regenerate plants having all or substantially all of the morphological and physiological characteristics of the alfalfa germplasm designated 'CW-R97-037-001' and having ATCC Accession No. PTA-7608.

This invention also provides a cell, cell culture, tissue and/or tissue culture of regenerable cells, the cells comprising genetic material from the alfalfa germplasm named 'CW-R97-037-005', wherein the cells regenerate plants having all or substantially all of the morphological and physiological characteristics of the alfalfa germplasm designated 'CW-R97-037-005' and having ATCC Accession No. PTA-7607. Using standard alfalfa breeding methods well know to one skilled in the art, the newly-developed alfalfa clones (e.g., CW-R97-037-001 and CW-R97-037-005) can be used to produce new alfalfa genotypes having improved somatic embryogenesis and other agronomic and economically beneficial traits (e.g., improved standability, rapid recovery, and/or later fall dormancy).

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

I. OVERVIEW OF THE INVENTION

Various factors are important for the efficient transformation of crop plants. Adventitious shoot regeneration from explants amenable to transformation is one of the most important. Numerous reports cite differences between genotypes within a species in the ability to regenerate shoots and further indicate that the developmental processes reflected by in vitro response are genetically controlled. The present invention is directed to the development of agronomically adapted alfalfa plants with improved somatic embryogenesis and methods for identifying and isolating such plants. Furthermore, the improved alfalfa plants of the present invention are directed to the production of transgenic alfalfa plants with adaptation, productivity, winterhardiness, and disease resistance.

II. DEFINITIONS

As used herein, the term "alfalfa" means any *Medicago* species, including, but not limited to, *M. sativa, M. murex, M. falcata, M. prostrata* and *M. truncatula*. Thus, as used herein, the term "alfalfa" means any type of alfalfa including, but is not limited to, any alfalfa commonly referred to as cultivated alfalfa, diploid alfalfa, glanded alfalfa, purple-flowered alfalfa, sickle alfalfa, variegated alfalfa, wild alfalfa, or yellow-flowered alfalfa.

As used herein, the term "transformation" means the transfer of nucleic acid (i.e., a nucleotide polymer) into a cell. As used herein, the term "genetic transformation" means the transfer and incorporation of DNA, especially recombinant DNA, into a cell.

As used herein, the term "transgenic" means cells, cell cultures, plants, and progeny of plants which have received a foreign or modified gene by one of the various methods of transformation, wherein the foreign or modified gene is from the same or different species than the species of the plant receiving the foreign or modified gene.

As used herein, the term "callus" refers to a clump of undifferentiated plant cells that are capable of repeated cell division and growth, and in some species, can be induced to form a whole plant.

As used herein, the term "somatic tissues" refers to tissues not including germ cells or gametes. Somatic tissues are composed of vegetative tissues and cells.

As used herein, the term "somatic embryogenesis" refers to the process of embryo initiation and development from vegetative or non-gametic cells. The embryos from a given tissue source are presumed to be genetically identical.

As used herein, the term "explant" refers to a piece of tissue taken from a donor plant for culturing.

III. SEED DEPOSITS

On May 22, 2006, at least 2,500 seeds of each of two different alfalfa germplasms were deposited under the conditions of the Budapest Treaty with the American Type Culture Collection (ATCC), 10801 University Blvd., Manassas, Va. 20110-2209. The following two seed deposits are exemplary of the instant invention:

Seed of alfalfa germplasm designated 'CW-R97-037-001' has been given ATCC No. PTA-7608.

Seed of alfalfa germplasm designated 'CW-R97-037-005' has been given ATCC No. PTA-7607.

With the exception permitted as specified in 37 C.F.R. §1.808(b), all restrictions on the public availability of ATCC Nos. PTA-7608 and PTA-7607 will be irrevocably removed upon the granting of the patent.

IV. SOMATIC EMBRYOGENESIS

Somatic embryogenesis is an important pathway for the regeneration of plants from cell culture systems and a method commonly used in large scale production of plants and synthetic seeds (Stuart et al. 1987). The techniques to form somatic embryos using only induction and regeneration steps was first described in alfalfa 33 years ago (Saunders & Bingham, 1972). In somatic (asexual) embryogenesis, embryo-like structures, which can develop into whole plants in a way analogous to zygotic embryos, are formed from somatic tissues. Somatic embryos are bipolar structures, having both a shoot and root pole, arising from sporophytic cells that have no vascular connection with the maternal tissue (Haccius, B. 1978). These somatic embryos can be produced either directly or indirectly. In direct somatic embryogenesis, the embryo is formed directly from a cell or small group of cells without the production of an intervening callus. In indirect somatic embryogenesis, callus is first produced from the explant. Embryos can then be produced from the callus tissue or from a cell suspension produced from that callus.

Somatic embryogenesis is one of a number of methods known in the art for the propagation of desirable species or varieties of plants. There are many advantages which favor somatic embryogenesis as a propagative method of choice. One advantage is that a plant which has a known and desirable phenotype can be chosen as the source of cells, and, in accordance with somatic embryogenesis techniques, these cells can be rapidly cultured into many genetically uniform embryos. The resulting embryos can then be cultivated into entire plants possessing roots and shoots. Thus, in accordance with this technique, plants with the same desirable phenotype as the parent can be mass produced, potentially at costs comparable to and often more quickly and with better genetic uniformity than other propagative techniques such as, for example, the generation of field grown seed (U.S. Pat. No. 5,187,092).

Some of the other prospective advantages of somatic embryogenesis include the following (Ammirato, P. V. et. al 1983): plant regeneration is more efficient since somatic embryos are bipolar structures and germination is a one-step process; somatic embryogenesis enables the rapid production of a large number of uniform plants within a relatively short period of time; somatic embryos can be encapsulated and treated like normal seed (i.e., stored and shipped); somatic embryos could be used for long-term storage in germplasm banks because of inherent dormancy properties; somatic embryos produce secondary metabolites not produced by undifferentiated callus (Niedz, R. P., et al., Plant Cell Tiss. Org. Cult., 51:181-185 (1997)); and somatic embryogenesis is a biological phenomenon uniquely suited as a tool to study basic questions of plant growth and development and aseptic nature of regenerants formed in vitro is also useful in quarantine situations because such materials can be utilized for safe introduction of crops from one state or country to another (U.S. Pat. No. 6,692,963).

V. CELL AND TISSUE CULTURE OF ALFALFA

Plants, due to their sessile nature and long life span, have developed a greater ability to endure extreme conditions and predation than have animals. Many of the processes involved in plant growth and development adapt to environmental conditions. This plasticity allows plants to alter their metabolism, growth and development to best suit their environment. Particularly important aspects of this adaptation, as far as plant tissue culture and regeneration are concerned, are the abilities to initiate cell division from almost any tissue of the plant and to regenerate lost organs or undergo different developmental pathways in response to particular stimuli. When plant cells and tissues are cultured in vitro they generally exhibit a very high degree of plasticity, which allows one type of tissue or organ to be initiated from another type. In this way, whole plants can be subsequently regenerated. This regeneration of whole organisms depends upon the concept that all plant cells can, given the correct stimuli, express the total genetic potential of the parent plant.

When cultured in vitro, all the needs, both chemical and physical, of the plant cells have to be met by the culture vessel, the growth medium and the external environment (light, temperature, etc.). The growth medium has to supply all the essential mineral ions required for growth and development. In many cases (as the biosynthetic capability of cells cultured in vitro may not replicate that of the parent plant), it must also supply additional organic supplements such as amino acids and vitamins. Many plant cell cultures, as they are not photosynthetic, also require the addition of a fixed carbon source in the form of a sugar (most often sucrose). One other vital component that must also be supplied is water, the principal biological solvent. Physical factors, such as temperature, pH, the gaseous environment, light (quality and duration) and osmotic pressure, also have to be maintained within acceptable limits.

Cultures are generally initiated from sterile pieces of a whole plant. These pieces are termed 'explants', and may consist of pieces of organs, such as leaves or roots, or may be specific cell types, such as pollen or endosperm. Many features of the explant are known to affect the efficiency of culture initiation. Generally, younger, more rapidly growing tissue (or tissue at an early stage of development) is most effective. Main types of cultures include but not limited to callus cultures, cell-suspension cultures, protoplasts, root cultures, shoot tip and meristem culture, embryo culture and microspore culture. Whole plants are regenerated from these cultures. Two methods of plant regeneration are widely used in plant transformation studies, i.e. somatic embryogenesis and organogenesis. In somatic (asexual) embryogenesis, embryo-like structures, which can develop into whole plants in a way analogous to zygotic embryos, are formed from somatic tissues. Organogenesis relies on the production of organs, either directly from an explant or from a callus culture.

Further reproduction of the alfalfa plants of the present invention can occur by cell and tissue culture and regeneration, wherein the tissue regenerates plants having all or substantially all of the morphological and physiological characteristics of the alfalfa plants provided by the present invention. Thus, another aspect of this invention is to provide cells which upon growth and differentiation produce alfalfa plants with improved somatic embryogenesis, adaptation, productivity, winterhardiness, and disease resistance.

Yet another embodiment is a tissue culture of regenerable cells, where the cells include genetic material with improved somatic embryogenesis, adaptation, productivity, winterhardiness, and disease resistance. Some embodiments include such a tissue culture that includes cultured cells derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts.

In one embodiment, this invention provides cells which upon growth and differentiation produce alfalfa plants having all or substantially all of the physiological and morphological characteristics of alfalfa germplasm designated 'CW-R97-037-001' and 'CW-R97-037-005'.

In another such embodiment, the present invention includes an alfalfa plant regenerated from the above described tissue culture.

Methods of producing alfalfa plants from tissue culture are well known by the ordinary artisan. See, for example, Daniel C. W. Brown, HortScience 23(3):526-531 (1988); Bingham, E. T., Crop Science 15:719-721 (1975); Fuentes et al., Plant Cell, Tissue and Organ Culture 34:299-302 (1993); Hanson et al., Crop Science 27:1084 (1987); Ray et al., Crop Science 29:1545-1548 (1989); Seitz et al., In Vitro Cellular & Developmental Biology 24:1047-1052 (1988); Bingham et al., Alfalfa Tissue Culture, pages 903-929, In *Alfalfa and Alfalfa Improvement*, Hanson et al. (ed.), American Society of Agronomy, Monograph No. 29 (1988); and U.S. Pat. Nos. 5,324,646; 5,731,202; 5,908,974; 5,994,626; 6,127,599; 6,143,951; 6,359,195; 6,563,019 and 6,566,137, each of which is incorporated herein in their entirety.

Initiation of callus from immature anthers, immature ovaries, cotyledons, internode sections, and seedling hypocotyls of alfalfa germplasm designated 'CW-R97-037-001' and 'CW-R97-037-005' can be achieved on Blaydes medium supplemented with various combinations and concentrations of kinetin (K), -naphthalene acetic acid (NAA), and 2,4-dichlorophenoxyacetic acid (2,4-D). See, for example, Saunders, J. W. and E. T. Bingham, Crop Science 12(6):804-808 (1972). Whole alfalfa plants can be produced from the callus tissue, wherein the alfalfa plants have the same or substantially the same morphological and physiological characteristics as the plant from which the calli were derived.

The foregoing detailed description has been given for clearness of understanding only and no unnecessary limitations should be understood therefrom as modifications will be obvious to those skilled in the art.

EXAMPLES

Example 1

Initial Screening to Identify Alfalfa Plants that Regenerate Somatic Embryos

Screening of 2,760 plants, elite clones from various breeding populations with excellent agronomic characters such as yield, forage quality, winter survival, persistence, disease resistance etc., was performed using a modification of the protocol developed by Eltjo G. M. Meijer and Daniel C. W. Brown (Physiol. Plantarum 69: 591-596 (1987)). The explant tissues were evaluated at 40 days for both the production of healthy callus and the production of somatic embryos. Comparisons were made to highly regenerable embryogenic clones, Regen SY27 and VS 154-2, both of which are embryogenic clones used for transformation by those skilled in the art and both of which have poor agronomic adaptation. A total of 44 plants (1.6%) were identified that produced healthy callus and regenerated some somatic embryos.

The 44 plants were observed for leaf disease resistance and/or crown rot resistance when digging a clone for greenhouse use. The plants were also generally observed for basic agronomic traits associated with adaptability, such as standability, recovery, yield, forage quality, winter survival and persistence.

Nineteen plants (listed in Table 1) were identified that combined production of somatic embryos with adaptation, productivity, winterhardiness, and disease resistance.

TABLE 1

Nineteen potential Cycle-0 plants selected for regeneration of somatic embryos.

| Clone | Source | Pedigree | Description |
|---|---|---|---|
| C96-0470 | D2-ELITE | S94 | 1252 RN |
| C96-0670 | D4-CA95 | 5040.1 | D4-Elite × PA-YT |
| C96-0752 | D3-CA95 | 5033.2 | 941-YT Px |
| C97-0040 | 96S-S96GHWIWS | 96-038 | GH 5032 Px |
| C97-0081 | 96S-S96GHWIWS | 96-038 | GH 5032 Px |
| C97-0083 | 96S-S96GHWIWS | 96-040-22 | D3-Elite × GH-Elite |
| C97-0086 | 96S-S96GHWIWS | 96-038 | GH 5032 Px |
| C97-0215 | 95F-RNGHWIWS | 5032 | (GH F1-D2 Px) & (GH-F1-D3 Px) |
| C97-0486 | 96S-CageCAWL | 96-038 | GH 5032 Px |
| C97-0801 | 94S-YTMNOW | 3408 | 93-5; 9000-YT-MN4 |
| C97-0829 | 94S-YTWIMT | 3414 | 900YT-185 |
| C97-0839 | 94S-YTMNOW | 3414 | 900YT-185 |
| C97-0881 | 94S-YTWIMT | 3433 | 91N-MD × 900YT-PA |
| C97-0884 | 94S-YTWIMT | 3449 | ELITE × 900YT-PA |
| C97-1407 | 94S-C94WISP | C91-938 | C90 Apn |
| C97-1483 | 95S-S95sWIWS | 95-58 | 941YT Px |
| C97-1485 | 95S-S95sWIWS | 4000-VW | 4000-VW |

TABLE 1-continued

Nineteen potential Cycle-0 plants selected for regeneration of somatic embryos.

| Clone | Source | Pedigree | Description |
|---|---|---|---|
| C97-1508 | 95S-S95nWIWS | 3000-NEM | 3000-NEM |
| C97-2239 | 96S-CageCAWL | 95–96 GH-ELITE | 95F-RNGH 5032-12 |

Example 2

Breeding for Alfalfa Plants with Improved Somatic Embryogenesis: Cycle-0

Seven clones, each found to produce somatic embryos in initial screening, were chosen as parents for a crossing program. Table 2 provides a list of the chosen clones. These seven parents were mated in paired-plant crosses to produce 15 separate hybrid combinations. Numerous seeds were produced within each cross and five randomly chosen seeds were planted from each cross.

Petioles from each of the seven parents (Table 2) and the five progeny plants per cross were collected and surface sterilized in 500 ml of 70% ethanol for one minute, and then transferred to 500 ml of 20% bleach (containing 0.5 ml of Tween 20) for 20 minutes. The petiole tissues were then rinsed with 500 ml of sterile water three times. The sterile petiole tissues were aseptically cut in four to six mm segments. Five petiole segments were inoculated onto Murashige and Skoog basic medium (MS-1)(pH=5.7-5.8) with two growth regulators: 33.0 µM 2,4-D and 5 µM Kinetin in 100× 15 mm plastic petri dishes. A completely random experimental design with seven replications was used. The entire experiment was repeated. The sterile petiole segments were incubated on MS-1 medium 10 days at 27° C. on a light rack (16 hr day). At 10 days, the petioles were transferred to new petri dishes containing Murashige and Skoog Basic Medium with no growth regulators (MS-2) for 30 days. The explant tissues were scored at 10, 20, 30, and 40 days for the following characteristics: size, color, vitrification, anthocyanin pigment, necrosis, and the number of embryos formed. Five explants (petioles) per genotype (or plant) per cross and 5 explants per genotype from the original plants that were screened were used in these experiments. Data for callus production and embryo regeneration of the parents chosen to represent the Cycle-0 population are listed in Table 2.

TABLE 2

Selected parent plants for Cycle-0 Crosses (Data collected at Day 40)

| Clone | Source | Pedigree | Callus Size (mm) Mean ± SE | # Embryos |
|---|---|---|---|---|
| C96-0670 | D4-CA95 | 5040.1 | 7.15 ± 0.34 | 1.31 ± 0.54 |
| C96-0752 | D3-CA95 | 5033.2 | 6.79 ± 0.44 | 0.00 ± 0.00 |
| C97-0081 | 96S-S96GHWIWS | 96-038 | 6.37 ± 0.90 | 0.00 ± 0.00 |
| C97-0215 | 95F-RNGHWIWS | 5032 | 8.69 ± 0.60 | 0.00 ± 0.00 |
| C97-0801 | 94S-YTMNOW | 3408 | 7.92 ± 0.40 | 0.08 ± 0.08 |
| C97-0881 | 94S-YTWIMT | 3433 | 9.57 ± 0.57 | 1.00 ± 0.49 |
| C97-1483 | 95S-S95sWIWS | 95-58 | 7.33 ± 0.38 | 0.00 ± 0.00 |

Data for callus production and embryo regeneration of the paired plant crosses between Cycle-0 parents resulting in Cycle-1 seed are listed in Table 3.

TABLE 3

Paired plant crosses between Cycle-0 parents resulting in Cycle-1 seed (Data collected at Day 40).

| Cross | Pedigree Female × Male | Callus Size | # Embryos |
|---|---|---|---|
| R97-001 | C96-0752 × C97-0881 | 8.68 ± 0.39 | 3.84 ± 0.87 |
| R97-002 | C97-0881 × C96-0752 | 6.39 ± 0.40 | 1.37 ± 0.56 |
| R97-003 | C97-0215 × C97-0881 | 7.88 ± 0.29 | 1.75 ± 0.56 |
| R97-004 | C97-0881 × C97-0215 | 7.47 ± 0.28 | 0.73 ± 0.26 |
| R97-005 | C97-0801 × C96-0752 | 8.20 ± 0.35 | 2.92 ± 0.66 |
| R97-006 | C96-0752 × C97-0801 | 9.29 ± 0.25 | 7.76 ± 1.71 |
| R97-008 | C96-0752 × C97-0215 | 8.63 ± 0.28 | 0.96 ± 0.48 |
| R97-010 | C96-0752 × C97-1483 | 8.66 ± 0.33 | 1.68 ± 0.50 |
| R97-015 | C96-0670, C96-0752, C97-0081, C97-0215, C97-0881 Px | 6.58 ± 0.32 | 0.33 ± 0.19 |
| R97-020 | C97-0081 × C97-0881 | 7.01 ± 0.28 | 0.24 ± 0.15 |
| R97-021 | C97-0881 × C97-0081 | 8.81 ± 0.28 | 0.62 ± 0.42 |
| R97-022 | C96-0670 × C97-0881 | 9.02 ± 0.36 | 3.71 ± 0.73 |
| R97-028 | C97-0081 × C97-0215 | 6.63 ± 0.22 | 0.02 ± 0.02 |
| R97-037 | C97-0801 × C96-0670 | 9.11 ± 0.29 | 7.93 ± 1.21 |
| R97-038 | C97-1483 × C96-0670 | 8.36 ± 0.37 | 2.56 ± 0.70 |

The number of somatic embryos for individual progenies ranged from zero to 21 within the 15 crosses. For five of the 15 crosses done, 80% of the progenies tested exhibited embryo production. Only crosses R97-015 and R97-028 showed no improvement in progeny embryo production relative to its parents (Table 4).

TABLE 4

Number of Embryos at Day 40 by Plant within Cross

| Cross | Plant 1 Mean ± SE | Plant 2 Mean ± SE | Plant 3 Mean ± SE | Plant 4 Mean ± SE | Plant 5 Mean ± SE |
|---|---|---|---|---|---|
| R97-001 | 13.00 ± 4.53 | 7.86 ± 1.53 | 2.67 ± 0.94 | 0.00 ± 0.00 | 1.50 ± 0.52 |
| R97-002 | 0.00 ± 0.00 | 5.45 ± 1.91 | 0.00 ± 0.00 | 0.09 ± 0.09 | 0.22 ± 0.22 |
| R97-003 | 0.70 ± 0.42 | 0.00 ± 0.00 | 0.10 ± 0.10 | 0.45 ± 0.31 | 6.50 ± 1.86 |
| R97-004 | 0.00 ± 0.00 | 3.86 ± 0.96 | 0.09 ± 0.09 | 0.36 ± 0.28 | 0.00 ± 0.00 |
| R97-005 | 0.00 ± 0.00 | 11.38 ± 1.74 | 1.55 ± 0.91 | 0.42 ± 0.34 | 2.75 ± 0.71 |
| R97-006 | 3.00 ± 0.71 | 0.11 ± 0.11 | 0.00 ± 0.00 | 6.18 ± 1.37 | 21.33 ± 3.82 |
| R97-008 | 1.50 ± 1.50 | 0.00 ± 0.00 | 4.00 ± 1.99 | 0.00 ± 0.00 | 0.00 ± 0.00 |
| R97-010 | 0.00 ± 0.00 | 0.70 ± 0.42 | 1.30 ± 1.30 | 4.36 ± 1.51 | 1.00 ± 0.45 |
| R97-015 | 0.00 ± 0.00 | 0.00 ± 0.00 | 1.00 ± 0.82 | 0.00 ± 0.00 | 1.14 ± 0.86 |
| R97-020 | 0.00 ± 0.00 | 0.44 ± 0.44 | 0.56 ± 0.44 | 0.00 ± 0.00 | 0.00 ± 0.00 |
| R97-021 | 0.09 ± 0.09 | 0.00 ± 0.00 | 6.25 ± 3.64 | 0.00 ± 0.00 | 0.00 ± 0.00 |
| R97-022 | 0.00 ± 0.00 | 8.71 ± 2.04 | 0.00 ± 0.00 | 1.21 ± 0.46 | 6.50 ± 1.44 |

TABLE 4-continued

Number of Embryos at Day 40 by Plant within Cross

| Cross | Plant 1 Mean ± SE | Plant 2 Mean ± SE | Plant 3 Mean ± SE | Plant 4 Mean ± SE | Plant 5 Mean ± SE |
|---|---|---|---|---|---|
| R97-028 | 0.00 ± 0.00 | 0.00 ± 0.00 | 0.00 ± 0.00 | 0.09 ± 0.09 | 0.00 ± 0.00 |
| R97-037 | 15.40 ± 2.22 | 0.50 ± 0.23 | 11.57 ± 2.38 | 0.11 ± 0.11 | 10.75 ± 2.91 |
| R97-038 | 2.30 ± 1.37 | 0.08 ± 0.08 | 2.73 ± 1.37 | 0.00 ± 0.00 | 6.90 ± 2.20 |

As shown in Table 4, several clones exhibited very high numbers of embryos after 40 days. Examples of such clones include the following: R97-001, Plant 1 (i.e., CW-R97-001-001); R97-006, Plant 5 (i.e., CW-R97-006-005); R97-037, Plant 1 (i.e., CW-R97-037-001); and R97-037, Plant 5 (i.e., CW-R97-037-005). R97-037, Plants 1 and 5 showed more classical development of bottle-shaped somatic embryos over the other clones and good embryo germination resulting in plants regenerating with normal shoot and root development. Their pedigree was more agronomically desirable and their embryo development was superior in tissue culture.

Example 3

New Alfalfa Genotype with Improved Somatic Embryogenesis and Salt Tolerance

Transgene 34S-AtNHX1, containing membrane transport protein (AtNHX1) that transports sodium ions (Na$^+$) into the vacuoles of plant cells in exchange for protons (H$^+$), can be introduced into leaf or petiole cells of the newly-developed alfalfa clones (CW-R97-037-001 and CW-R97-037-005) by Agrobacterium-mediated transformation. The resulting new alfalfa genotype will show improved somatic embryogenesis and also tolerate high levels of soil salinity.

Example 4

New Alfalfa Genotype with Improved Somatic Embryogenesis and Reduced Leaf Senescence Transgene PSAG12-IPT (ipt, a cytokinin biosynthetic gene from *Agrobacterium tumefaciens*, under the control of the promoter from a senescence-associated gene (SAG12)) can be introduced into leaf or petiole cells of the newly-developed alfalfa clones (CW-R97-037-001 and CW-R97-037-005) by Agrobacterium-mediated transformation. The resulting new alfalfa genotype will show improved somatic embryogenesis with reduced leaf senescence.

REFERENCES

1. Ammirato, P. V., Embryogenesis, In: Evans, E. A., Sharp, W. R., Ammirato, P. V., Yamada, Y., eds., (1983) Handbook of plant cell culture, Volume 1, Techniques for propagation and breeding, Macmillan Publishing Company 82-123
2. Haccius, B. (1978) "Question of unicellular origin of non-zygotic embryos in callus cultures" *Phytomorphology* 28:74-81
3. Saunders, J. W., and E. T. Bingham (1972) "Production of alfalfa plants from callus tissue" Crop Sci. 12: 804-808

What is claimed is:

1. An alfalfa clone designated 'CW-R97-037-001' and having ATCC No. PTA-7608 or designated 'CW-R97-037-005' and having ATCC No. PTA-7607.
2. A cell, tissue, seed, or whole plant of the alfalfa clone of claim 1.
3. A cell culture or tissue culture of the alfalfa clone of claim 1.
4. Pollen or an ovule of the alfalfa clone of claim 1.
5. A seed of an alfalfa plant pollinated by the pollen of claim 4 or regenerable parts of said seed.
6. An alfalfa plant produced by the seed of claim 2 or regenerable parts of said seed.
7. A tissue culture of regenerable cells, the cells comprising genetic material from an alfalfa plant of CW-R97-037-001, wherein the cells regenerate plants having all the morphological and physiological characteristics of a plant of CW-R97-037-001 the seed of which have been deposited and having ATCC Accession No. PTA-7608.
8. A tissue culture of regenerable cells, the cells comprising genetic material from an alfalfa plant of CW-R97-037-005, wherein the cells regenerate plants having all the morphological and physiological characteristics of a plant of CW-R97-037-005 the seed of which have been deposited and having ATCC Accession No. PTA-7607.
9. A method for producing alfalfa seed comprising crossing alfalfa clone 'CW-R97-037-001' and having ATCC No. PTA-7608 with itself or another alfalfa clone, and harvesting the resultant seed.
10. The method of claim 9, further comprising growing the resultant seed to produce one or more progeny alfalfa clones.
11. The progeny alfalfa clones produced by the method of claim 10, wherein the progeny alfalfa clones are capable of producing at least the same number of embryos from somatic embryogenesis compared to the number of embryos produced by 'CW-R97-037-001', wherein the somatic embryogenesis of the progeny alfalfa clones and 'CW-R97-037-001' were conducted using the same or similar procedures.
12. A method for producing alfalfa seed comprising crossing alfalfa clone 'CW-R97-037-005' and having ATCC No. PTA-7607 with itself or another alfalfa clone, and harvesting the resultant seed.
13. The method of claim 12, further comprising growing the resultant seed to produce one or more progeny alfalfa clones.
14. The progeny alfalfa clones produced by the method of claim 13, wherein the progeny alfalfa clones are capable of producing at least the same number of embryos from somatic embryogenesis compared to the number of embryos produced by 'CW-R97-037-005', wherein the somatic embryogenesis of the progeny alfalfa clones and 'CW-R97-037-005' were conducted using the same or similar procedures.

* * * * *